(12) United States Patent
Khouri et al.

(10) Patent No.: US 11,464,515 B2
(45) Date of Patent: Oct. 11, 2022

(54) DEVICES AND METHODS FOR WOUND CLOSURE

(71) Applicant: Lipocosm LLC, Key Biscayne, FL (US)

(72) Inventors: Roger K. Khouri, Key Biscayne, FL (US); Khalil R. Khouri, Key Biscayne, FL (US)

(73) Assignee: Liopcosm, LLC, Key Biscayne, FL (US)

( * ) Notice: Subject to any disclaimer, the term of this patent is extended or adjusted under 35 U.S.C. 154(b) by 208 days.

(21) Appl. No.: 16/882,443

(22) Filed: May 23, 2020

(65) Prior Publication Data

US 2020/0367889 A1 Nov. 26, 2020

Related U.S. Application Data

(60) Provisional application No. 62/852,288, filed on May 23, 2019.

(51) Int. Cl.
*A61B 17/08* (2006.01)
*A61B 17/00* (2006.01)

(52) U.S. Cl.
CPC .... *A61B 17/08* (2013.01); *A61B 2017/00796* (2013.01); *A61B 2017/081* (2013.01)

(58) Field of Classification Search
CPC .......... A61B 17/08; A61B 2017/00796; A61B 2017/081; A61B 2017/283; A61B 17/29;
(Continued)

(56) References Cited

U.S. PATENT DOCUMENTS

| | | | |
|---|---|---|---|
| 6,007,552 A | * | 12/1999 | Fogarty .................. A61B 17/02 606/157 |
| 2012/0143241 A1 | * | 6/2012 | Ray ...................... A61B 17/062 606/205 |

(Continued)

FOREIGN PATENT DOCUMENTS

CN 109009395 B * 10/2020 ........... A61B 17/282

OTHER PUBLICATIONS

Khouri, KS et al. Percutaneous Mesh Expansion: A Regenerative Wound Closure Alternative. Plast Reconstr Surg, vol. 141, No. 2, Feb. 2018, pp. 451-457 [pdf online], [retrieved on Feb. 8, 2022], Retrieved from the Internet <URL:https://journals.lww.com/plasreconsurg/Fulltext/2018/02000 > (Year: 2018).*

(Continued)

*Primary Examiner* — Katherine H Schwiker
*Assistant Examiner* — Serenity A Miller
(74) *Attorney, Agent, or Firm* — Neil D. Gershon

(57) ABSTRACT

The present disclosure provides methods and devices for wound closure. In some exemplary embodiments, a tissue approximation device is provided. In some embodiments, the tissue approximation device includes a first scissors arm having a proximal end and a distal end and a second scissors arm having a proximal end and a distal end. In some embodiments, the second scissors arm is connected to the first scissors arm at a pivot point. In some embodiments, the tissue approximation device further includes a first rake member connected to the distal end of the first scissors arm via a first articulating joint. In some embodiments, the first rake member includes a plurality of hooks configured to grip tissue.

14 Claims, 9 Drawing Sheets

(58) Field of Classification Search
CPC ... A61B 17/28; A61B 17/282; A61B 17/2833; A61B 2017/2837
USPC ................................ 606/215, 216, 218, 190
See application file for complete search history.

(56) References Cited

U.S. PATENT DOCUMENTS

2012/0296172 A1* 11/2012 Raven, III ......... A61B 17/0206
600/231
2014/0257035 A1* 9/2014 Blain ................. A61B 17/0206
600/104

OTHER PUBLICATIONS

Khouri, R., Khouri, K., Khouri, R. (2016). Percutaneous mesh expansion: A new wound closure alternative. AAPS. Retrieved Feb. 8, 2022, from <URL:https://meeting.aaps1921.org/abstracts/2016/31.cgi> (Year: 2016).*

* cited by examiner

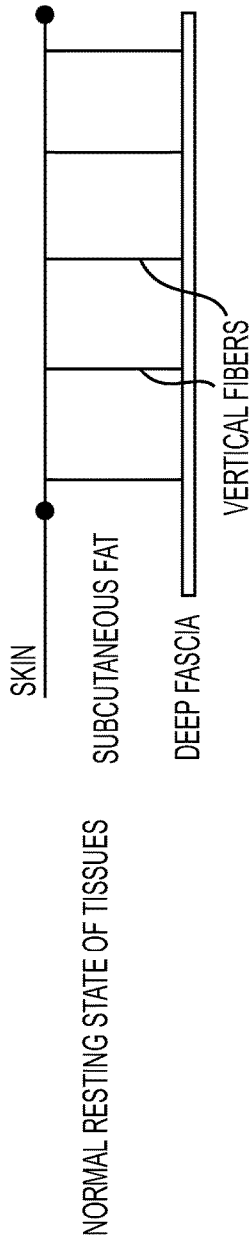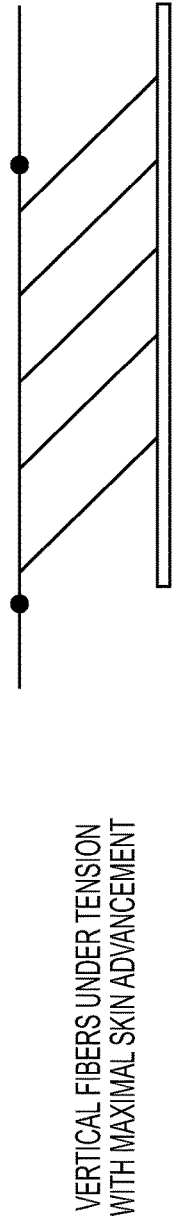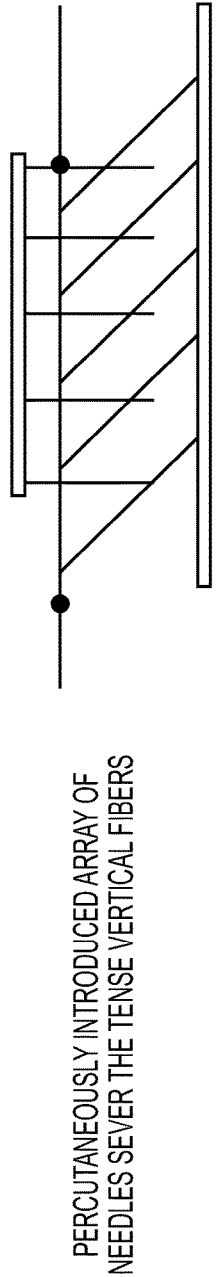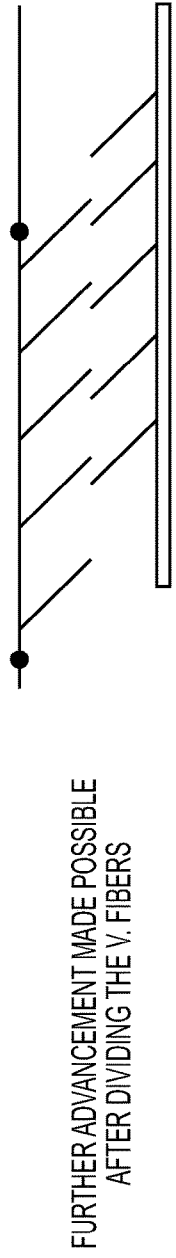
FIG. 1A — NORMAL RESTING STATE OF TISSUES (SKIN, SUBCUTANEOUS FAT, DEEP FASCIA, VERTICAL FIBERS)
FIG. 1B — VERTICAL FIBERS UNDER TENSION WITH MAXIMAL SKIN ADVANCEMENT
FIG. 1C — PERCUTANEOUSLY INTRODUCED ARRAY OF NEEDLES SEVER THE TENSE VERTICAL FIBERS
FIG. 1D — FURTHER ADVANCEMENT MADE POSSIBLE AFTER DIVIDING THE V. FIBERS

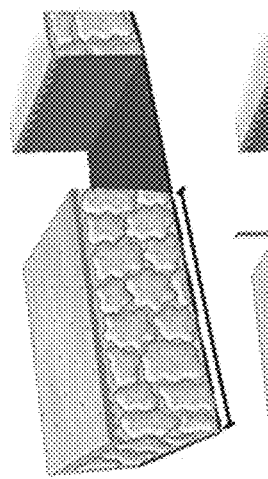
FIG. 2A Wound defect placed under tension
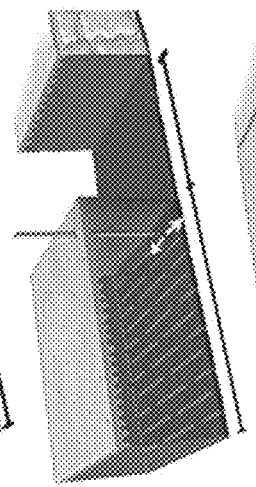
FIG. 2B Oscillating needle inflicting a pattern of staggered alternating slits in the tensed tissue
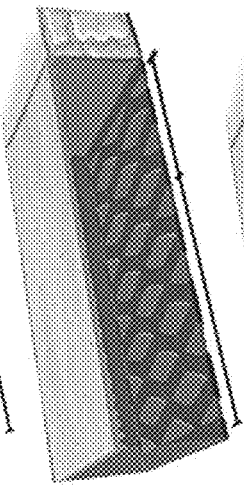
FIG. 2C Mesh expansion of the slits allows wound edges to advance
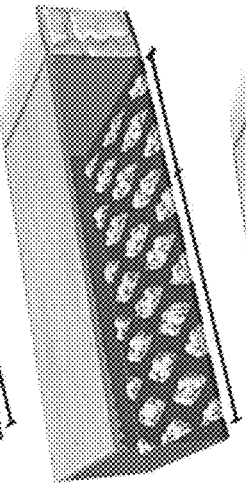
FIG. 2D Healing tissue regenerates and fills the gaps between slits
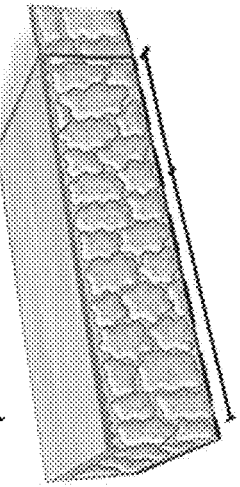
FIG. 2E Tensionless closure of wound defect by mesh expansion of tensed wound edges

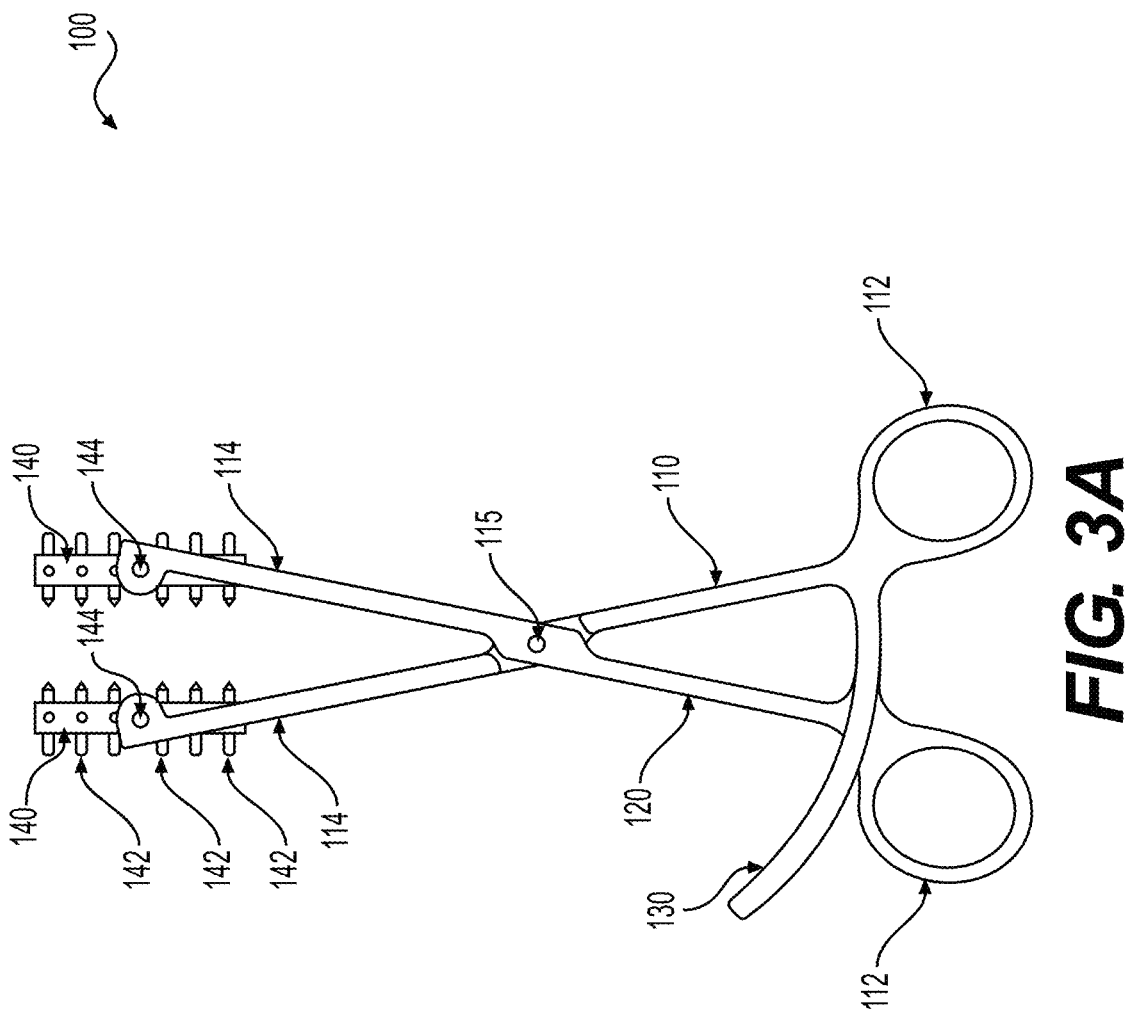

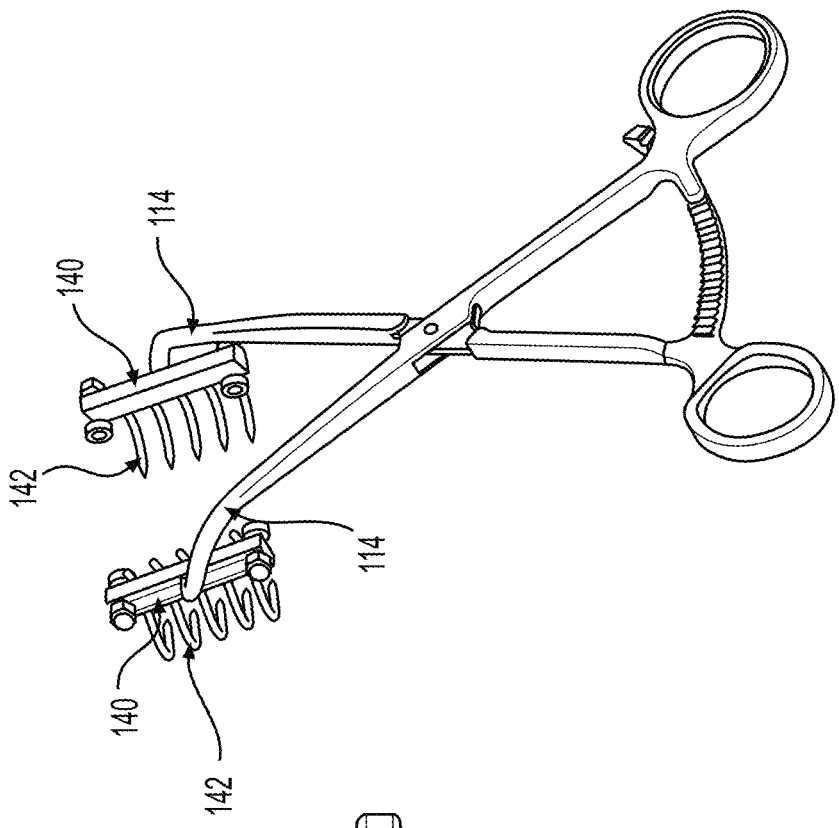
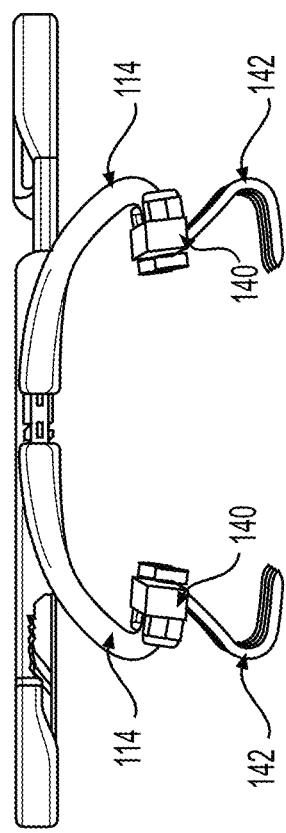
FIG. 4B
FIG. 4A

DEVICES AND METHODS FOR WOUND CLOSURE

CROSS-REFERENCE TO RELATED APPLICATION

This application claims the benefit of priority of U.S. Provisional Patent Application No. 62/852,288, filed May 23, 2019, which is incorporated herein by reference.

TECHNICAL FIELD

The present disclosure relates to surgical devices and methods for wound closure and corresponding methods for performing reconstructive surgical procedures.

BACKGROUND

Surgical wounds can be left to heal by themselves (secondary intention healing), or they can be closed surgically. Secondary intention healing of a wound can take weeks to months depending on the size and location of the wound. In many cases, scars are formed after healing of the wound. In some situations, surgical closure is preferred over secondary intention healing when it can accelerate the healing process, protect the underlying tissues (e.g., bone, cartilage, nerve), improve skin function by choosing the direction of skin tension on the wound edges (e.g., avoiding ectropion), and/or improve cosmesis by hiding the scar on the wound edges as much as possible.

Typical surgical techniques to close a wound include primary closure, skin graft, and flap tissue transfers. Large wounds with edges that cannot be approximated without applying excessive tension usually require skin grafts or flap tissue transfers for closure. However, these procedures often result in residual disfiguring scars, carry significant morbidity, and give the final appearance of a patch. Therefore, there is a need for devices and methods that allow for safe closure of large wounds without or with reduced residual scars.

SUMMARY

According to an exemplary embodiment of the present disclosure, a tissue approximation device is described. In some embodiments, the tissue approximation device includes a first scissors arm having a proximal end and a distal end and a second scissors arm having a proximal end and a distal end. In some embodiments, the second scissors arm is connected to the first scissors arm at a pivot point. In some embodiments, the tissue approximation device further includes a first rake member connected to the distal end of the first scissors arm via a first articulating joint. In some embodiments, the first rake member includes a plurality of hooks configured to grip tissue. In some embodiments, the tissue approximation device further includes a second rake member connected to the distal end of the second scissors arm via a second articulating joint. In some embodiments, the second rake member includes a plurality of hooks configured to grip tissue.

According to an exemplary embodiment of the present disclosure, a kit for closing a wound is described. In some embodiments, the kit includes a tissue approximation device and a meshing device. In some embodiments, the tissue approximation device is configured to apply tension to tissue in an area of interest for closing the wound. In some embodiments, the tissue approximation device includes a first scissors arm having a proximal end and a distal end and a second scissors arm having a proximal end and a distal end. In some embodiments, the second scissors arm is connected to the first scissors arm at a pivot point. In some embodiments, the tissue approximation device further includes a first rake member connected to the distal end of the first scissors arm via a first articulating joint. In some embodiments, the first rake member includes a plurality of hooks configured to grip tissue. In some embodiments, the meshing device includes at least one puncturing device configured to puncture the tissue.

According to an exemplary embodiment of the present disclosure, a method for closing a wound is described. In some embodiments, the method includes applying tension to tissue in an area of interest for closing the wound using a tissue approximation device. In some embodiments, the method further includes meshing the tissue while under the tension using a meshing device. In some embodiments, the method further includes releasing at least a portion of the tension. In some embodiments, the method includes bringing the wound edges together under tension using the tissue approximation device. In some embodiments, the method further includes relieving the tension by inflicting a staggered pattern of alternating punctures using the meshing device to mesh expand the restrictive tissue to achieve a tensionless closure of the wound defect.

Additional disclosure of the disclosed embodiments will be set forth in part in the description that follows.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain exemplary principles of certain disclosed embodiments as set forth in the accompanying claims.

BRIEF DESCRIPTION OF THE DRAWINGS

FIGS. 1A-1D illustrate an exemplary technique for releasing restrictive fibrous structures in tissue placed under tension.

FIGS. 2A-2E illustrate an exemplary technique for closing a wound defect, according to some embodiments of the present disclosure.

FIG. 3A illustrates an exemplary tissue approximation device, according to some embodiments of the present disclosure.

FIG. 4A illustrates a front view of an exemplary tissue approximation device, according to some embodiments of the present disclosure.

FIG. 4B illustrates a perspective view of the exemplary tissue approximation device of FIG. 4A.

DETAILED DESCRIPTION

Figure 3B:
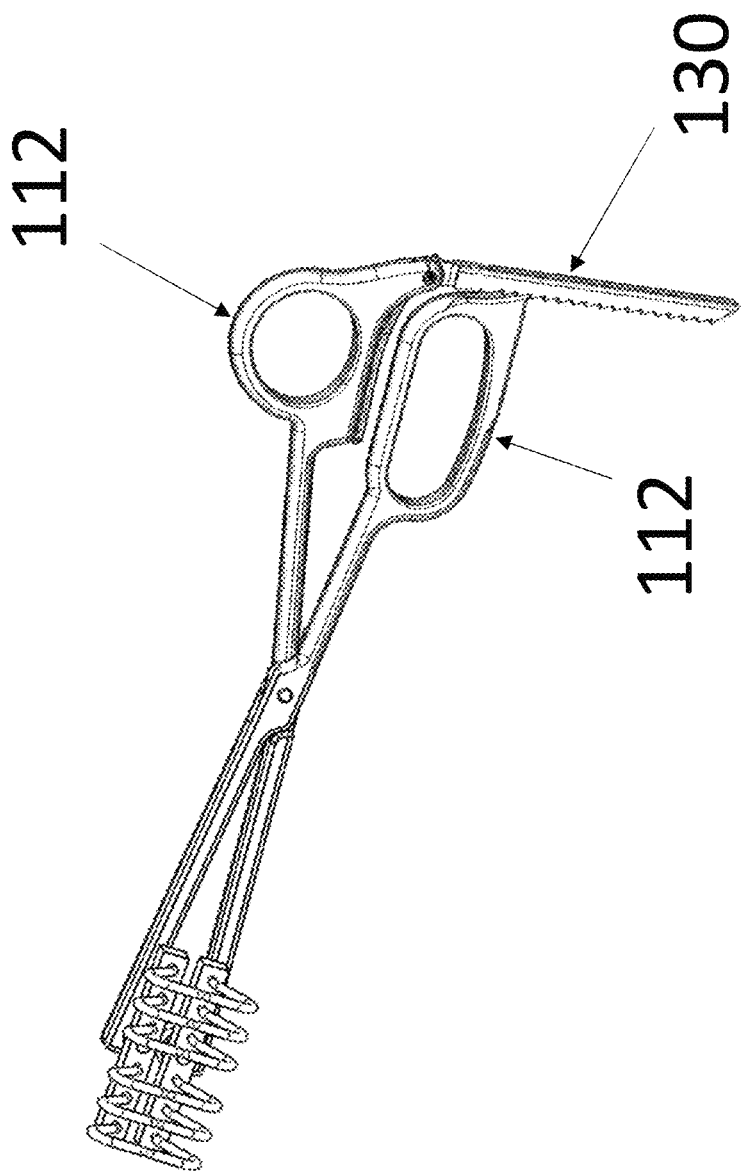
FIG. 3B illustrates an exemplary tissue approximation device, according to some embodiments of the present disclosure.

The devices and methods of the present disclosure use and/or enhance the regenerative ability of tissues to close wounds, do not require expensive equipment, and allow for minimal or at least reduced morbidity compared to existing devices and wound closing methods. In some embodiments, the present disclosure allows for the healing or closing of wounds without scars. In some embodiments, the present disclosure allows for the healing or closing of wounds without visible scars. In some embodiments, the present disclosure allows for the healing or closing of wounds with less scars than existing wound closure procedures do.

The inventors recognized that tissue can regenerate across tiny (e.g., 1 mm) gaps without forming a scar. The inventors further recognized that by creating a large number of these small gaps, wounds that would otherwise have required flaps or grafts can instead be closed by the approximation of scarless tissue regeneration.

According to some embodiments of the present disclosure, a method for wound closure is provided. In some embodiments, the method for wound closure uses a tissue approximation device to temporarily approximate the edges surrounding a wound and place the tissue in an area of interest under tension. As defined herein, the area of interest may include an area in the wound, an area surrounding the wound, or both. In some embodiments, a method for wound closure includes performing a surgical technique of percutaneous mesh expansion. In some embodiments, percutaneous mesh expansion is performed while the tissue in the area of interest is placed under tension. In some embodiments, percutaneous mesh expansion is performed using a sharp needle or a meshing device comprising an array of needles.

The following section describes percutaneous mesh expansion according to some embodiments of the present disclosure. Various features and functions of the meshing device and the tissue approximation device according to some embodiments of the present disclosure are described in the sections that follow.

Percutaneous Mesh Expansion (PME)

The inventor developed PME as a regenerative wound closure procedure to reduce or minimize residual scars after a wound heals. The inventor developed this procedure based, at least in part, upon a discovery that needle puncture wounds in the 1 mm range, such as wounds caused by insertion of intravenous lines, typically heal without residual scars. In some embodiments, PME is performed by applying punctures to the tissue in an area of interest to release the restrictive fibrous structures in the tissue. The release of the restrictive fibrous structures allows the tissue to expand and facilitate the advancement of the tissue towards the wound, thereby closing the wound. In some embodiments, the punctures are applied in the form of stacked rows or arrays of punctures to the tissue.

As described herein, the term "tissue" refers to any types of soft tissue at and/or surrounding a wound site that that connect, support, or surround structures and organs of the body, not being hard tissue, such as bone. Tissue may include muscles, tendons, fat, fascia, skin, or any other type of soft tissue. As used herein, the term "meshing" refers to applying one or more stacked rows or arrays of punctures to a tissue to release the restrictive fibrous structures in the tissue. As used herein, the term releasing the restrictive fibrous structures in the tissue may include severing, nicking, or cutting the restrictive fibrous structures in the tissue. It is also recognized that needles can release the restrictive fibrous structures in the tissue that is placed under tension while sparing other structures in the tissue, such as nerves or blood vessels.

The inventor further discovered that punctures are more likely to release the restrictive fibrous structures in a tissue when the tissue is placed under tension. FIGS. 1A-1D illustrate an example of releasing vertical fibers by percutaneously meshing or puncturing a tissue placed under tension. As illustrated in FIG. 1A, restrictive fibrous structures connect the skin and the deep immobile tissue layers, such as the fascia underneath. These restrictive fibrous structures can be collectively called the subcutaneous aponeurosis.

As illustrated in FIG. 1B, the restrictive fibrous structures impose a natural laxity limit to how much tissue can normally be advanced. As illustrated in FIG. 1C, applying tension to the skin to maximize advancement of the skin within the natural laxity limit of the subcutaneous aponeurosis places the restrictive fibrous structures under tension, rendering them more susceptible to being released by percutaneous meshing or punctures. When these restrictive fibrous structures are released as illustrated in FIG. 1D, tension is then reduced or released, and the tissue can then expand and advance beyond the natural laxity limit of the subcutaneous aponeurosis.

The inventor discovered that the release of the restrictive fibrous structures creates a fibrous vascularized scaffold with interstices that are later filled in by new tissue generated by the natural regenerative abilities of tissue. The filling of the interstices increases the volume of the tissue and causes the tissue to expand in the fibrous vascularized scaffold. Such tissue expansion further facilitates the advancement of tissue at and/or towards the wound. Therefore, the release of the restrictive fibrous structures allows the wound to be filled with naturally regenerated tissue instead of scar tissue to eventually close the wound. This process of tissue regeneration and expansion in a fibrous scaffold with interstices created by meshing the tissue is referred herein as "mesh expand" or "mesh expansion."

FIGS. 2A-2E illustrate an exemplary technique for closing a wound defect. FIG. 2A illustrates that the subcutaneous aponeurosis can restrict the approximation of the tightened wound edges. FIG. 2B illustrates using a needle to inflict a staggered pattern of alternating slits in the tissue under tension. In some embodiments, the needle is a needle with at least one cutting edge. In some embodiments, the needle is oscillated or moved back and forward to create a slit after punctuation. The slits created by the needle may release all or some of the tension in the tissue. FIGS. 2C and 2D illustrate that the slits allow the tissue to mesh expand by regenerating new tissue that fills the gaps between the slits. In some embodiments, the slits allow the tissue to mesh expand around and/or towards the wound edges. In some embodiments, the slits allow the tissue at and/or around the wound edges to mesh expand, thereby approximating the wound edges to achieve a tensionless closure.

The inventor further discovered that the size of the punctures and their spacing can affect the amount of tissue regeneration and/or expansion that can be achieved. Excessive meshing or punctures could destroy the local circulation, leading to ischemia and necrosis. Excessive meshing or punctures could also tear the deeper tissues and destroy the integrity of the fibrous vascularized scaffold, leading to the creation of undesirable cavities in the tissue. Therefore, the inventor found that the meshing ratio, that is the ratio of the amount of tissue that is punctured to the total amount of the tissue in an area of interest, needs to be judiciously determined to maintain a fibrous scaffold with sufficient capillary circulation while still allowing for tissue regeneration. In some embodiments, a meshing ratio ranging from 20% to 40% is used for meshing the tissue in an area of interest.

In some embodiments, the punctures are applied in a meshing pattern designed and gauged to create interstices for the tissue to naturally expand into using its regenerative abilities. In some embodiments, the punctures are applied in a meshing pattern designed and gauged to provide a recipient scaffold with interstices for receiving a regenerative graft material. In some embodiments, the meshing pattern includes an array of punctures spaced apart by 1 mm to 10 mm. In some embodiments, the meshing pattern includes an array of punctures arranged in one or more staggered rows. In some embodiments, the meshing pattern includes an array of punctures arranged in 2 to 6 staggered rows. In some embodiments, each puncture wound of the meshing pattern has a width or a diameter of 1 mm to 1.5 mm. In some embodiments, the interstices created by the punctures are filled by regenerated tissue over a period of healing time. In some embodiments, the interstices created by the punctures are filled with a material having regenerative potential. In some embodiments, the material having regenerative potential may be platelet rich plasma, physiological solutions containing growth factors, adipose tissue, stem cells or other types of cells, autografts, allografts, or a combination thereof.

In some embodiments, the interstices of the fibrous vascularized scaffold created by the meshing or puncturing provide a favorable graft to recipient interface where regenerative graft material can survive. Therefore, in some embodiments, the material having regenerative potential is a regenerative graft material. The regenerative graft material may be a man-made material, a naturally occurring material, or a material derived from a naturally occurring material. For example, the regenerative graft material may include an adipogenic material, a material derived from fat cells, a material derived from fat tissue, liposuctioned tissue, a material derived from liposuctioned tissue, adipose cells, stem cells, growth factors, or a selected combination thereof. The stem cells may include adipose-derived stems cells. The adipogenic material, material derived from fat tissue (whether autogenous or from allografts), liposuctioned tissue, or material derived from liposuctioned tissue may include adipose cells, adipose-derived stems cells, and/or growth factors.

In some embodiments, PME is performed to close a wound of large size. In some embodiments, the size of the wound ranges from 3 cm to 15 cm. In some embodiments, the size of the wounds that can be closed with this technique is limited by the available amount of normal peripheral tissue that can be safely meshed. In some embodiments, PME is performed to close the wound of a plastic surgery reconstruction site. In some embodiments, PME is performed to close the wound of a graft material harvesting site, such as a liposuction site. In some embodiments, PME is performed to close the wound of a reconstruction site that receives a graft material, such as a lipografting site. For example, PME may be performed to close the wound of a breast reconstruction site that receives a graft material. In some instances, PME is used to close the defect created by a transferred or advanced flap.

Performing the surgical technique of PME may include a series of procedures. In some embodiments, local or general anesthesia is performed. For example, tumescent epinephrine or lidocaine anesthesia may be performed at and/or around the wound. In some embodiments, after anesthesia is performed, the wound edges or the tissue in an area of interest are temporarily approximated and placed under tension using a tissue approximation device. Embodiments of the tissue approximation device are described in detail further below. Then, PME is performed to the tissue in the area of interest to release the restrictive fibrous structures in the tissue. In some embodiments, the area of interest for applying the PME is predetermined based on one or more considerations, which may include the size of the wound, the nature of the tissue in the area of interest, and the location of the wound. In some embodiments, a meshing pattern is predetermined based on one or more of these considerations.

In some embodiments, wound closure is performed without using the tissue approximation device to apply tension. The wound edges or the tissue in an area of interest are alternatively temporarily approximated with sutures under tension, such as retention sutures with subsequent full relief of the tension by the meshing, to facilitate perfusion of the edges and normal wound healing. In some embodiments, wound closure is performed before tension is fully relieved. In some embodiments, such wound closure is performed using the surgical technique of primary closure.

In some embodiments, the surgical technique of PME is performed to close the wound of a site for harvesting a graft material. In these embodiments, before performing PME, a graft material is retrieved from the wound. In some embodiments, the surgical technique of PME is performed to close the wound of a reconstructive site for receiving a graft material. In these embodiments, before performing PME, a graft material is injected or otherwise placed into the wound. In some embodiments, after performing PME, a material having regenerative potential is injected into the tissue in the area of interest to facilitate the expansion and advancement of the tissue for closing the wound.

Meshing Device

In some embodiments, PME is performed using a meshing device. In some embodiments, the meshing device includes at least one puncturing device. In some embodiments, the meshing device includes a supporting framework, and the at least one puncturing device is mounted on the supporting framework.

In some embodiments, the puncturing devices are needles. In some embodiments, the needles are cutting needles or hypodermic needles. In some embodiments, the puncturing devices are pins or rods with sharp cutting tips. In some embodiments, the puncturing devices are configured to be mounted on a supporting framework to have the same angle of penetration. In other embodiments, the puncturing devices are configured to be mounted on the supporting framework to have different angles of penetration.

In some embodiments, the puncturing devices have the same length. In such embodiments, the meshed tissue includes interstices distributed in one or two dimensions, which allows the expansion of a slice or a sheet of tissue. In other embodiments, the puncturing devices have different lengths. In such embodiments, the meshed tissue includes interstices distributed in three dimensions, which allows three-dimensional volumetric expansion of tissue. In some embodiments, the length of the puncturing devices ranges from 1 cm to 15 cm.

In some embodiments, the tissue mesher described in FIGS. 21-28 in International Patent Application No. PCT/US2013/039675 is used as the meshing device. International Patent Application No. PCT/US2013/039675 is incorporated herein by reference in its entirety.

Tissue Approximation Device

As described above, punctures are more likely to release the restrictive fibrous structures in the tissue in an area of interest when the tissue is placed under tension. Thus, in some embodiments, PME is performed after the tissue in the area of interest is placed under tension. In some embodiments, the tension is applied temporarily. Various methods may be used to place tissue under tension. According to some embodiments of the present disclosure, the tissue may be placed under tension generated by an internally or externally applied mechanical force. For example, a surgeon may insert retention sutures over protective bolsters, but this process takes time and consumes extra supplies. Alternatively, the surgeon may choose to use one of several commercially available tissue approximation devices. However, such devices are expensive and difficult to manipulate. Accordingly, some embodiments of the present disclosure provide a tissue approximation device that is more intuitive and ergonomic for surgeons to use than commercially available tissue approximation devices. Exemplary embodiments of the tissue approximation device are described below with reference to FIGS. 3A-6.

Figure 3C:
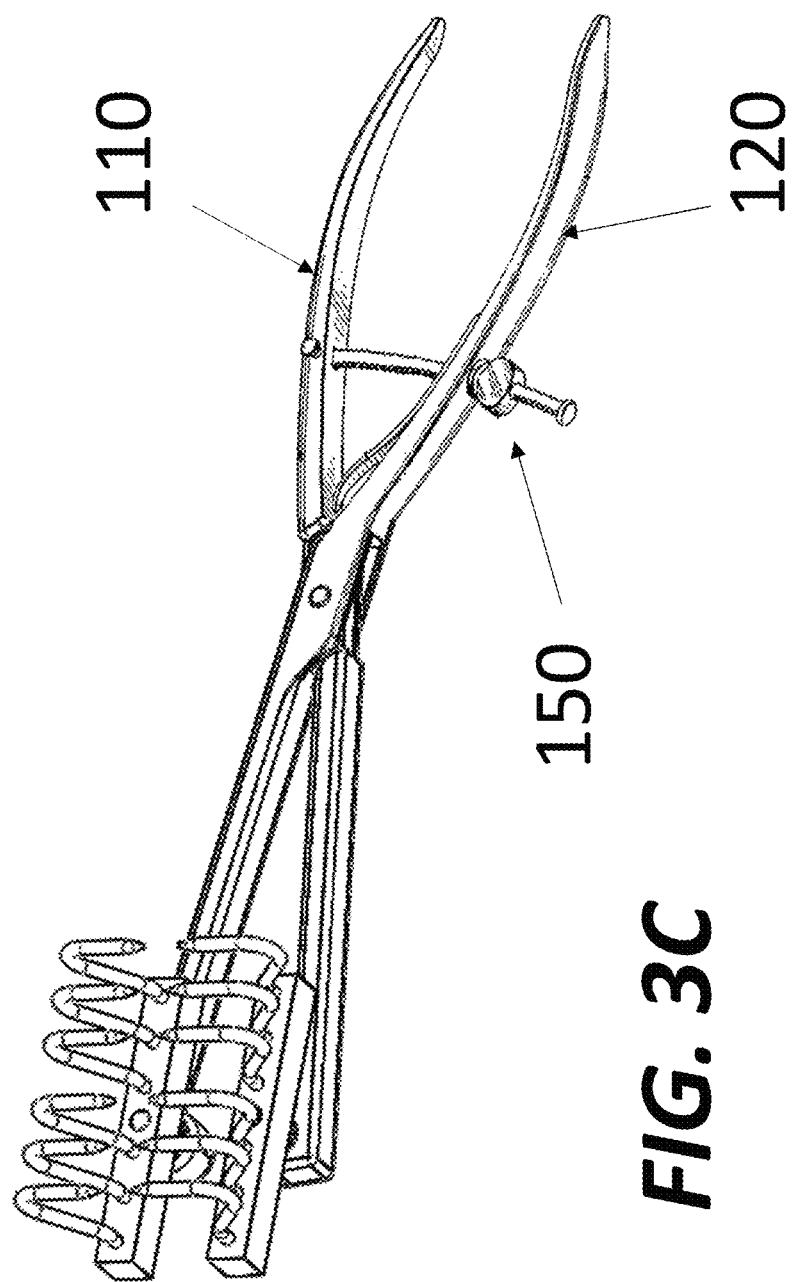
FIG. 3C illustrates an exemplary tissue approximation device, according to some embodiments of the present disclosure.

FIG. 3A is a schematic representation of a tissue approximation device 100, according to some embodiments of the present disclosure. As shown in FIG. 3A, in some embodiments, tissue approximation device 100 includes a first scissors arm 110 pivotally connected to a second scissors arm 120 at a pivot point 115 (also called a box lock). In some embodiments, the first and second scissors arms 110 and 120 each have a ring handle 112 at the proximal end. The ring handles 112 serve as finger grips. Tissue approximation device 100 can be closed by approximating or bringing together the ring handles 112, which in turn approximates or brings together the distal ends 114 of the first and second scissors arms 110 and 120. In some embodiments, the proximal ends of the first and second scissors arms 110 and 120 comprise straight or curved handles instead of the ring handles 112 to serve as finger grips. For example, as shown in FIG. 3C, the proximal ends the first and second scissors arms 110 and 120 comprise handles similar to the handles of a plier.

In some embodiments, a pivot bearing is mounted at pivot point 115 to form an axis of rotation of the relative movement between the first and second scissors arms 110 and 120 so that the scissors arms can pivot in a normal scissors or forceps fashion. In some embodiments, the pivot bearing is formed as a flanged shaft inserted into the first scissors arm 110 and second scissors arm 120. In some embodiments, the flanged shaft is a screw or a nail. In some embodiments, the flanged shaft has a short head that forms a flange and has a shank or a pin passing through the thickness of the first scissors arm 110 (and/or thickness of the second scissors arm 120) at the location of the pivot point 115.

Figure 3D:
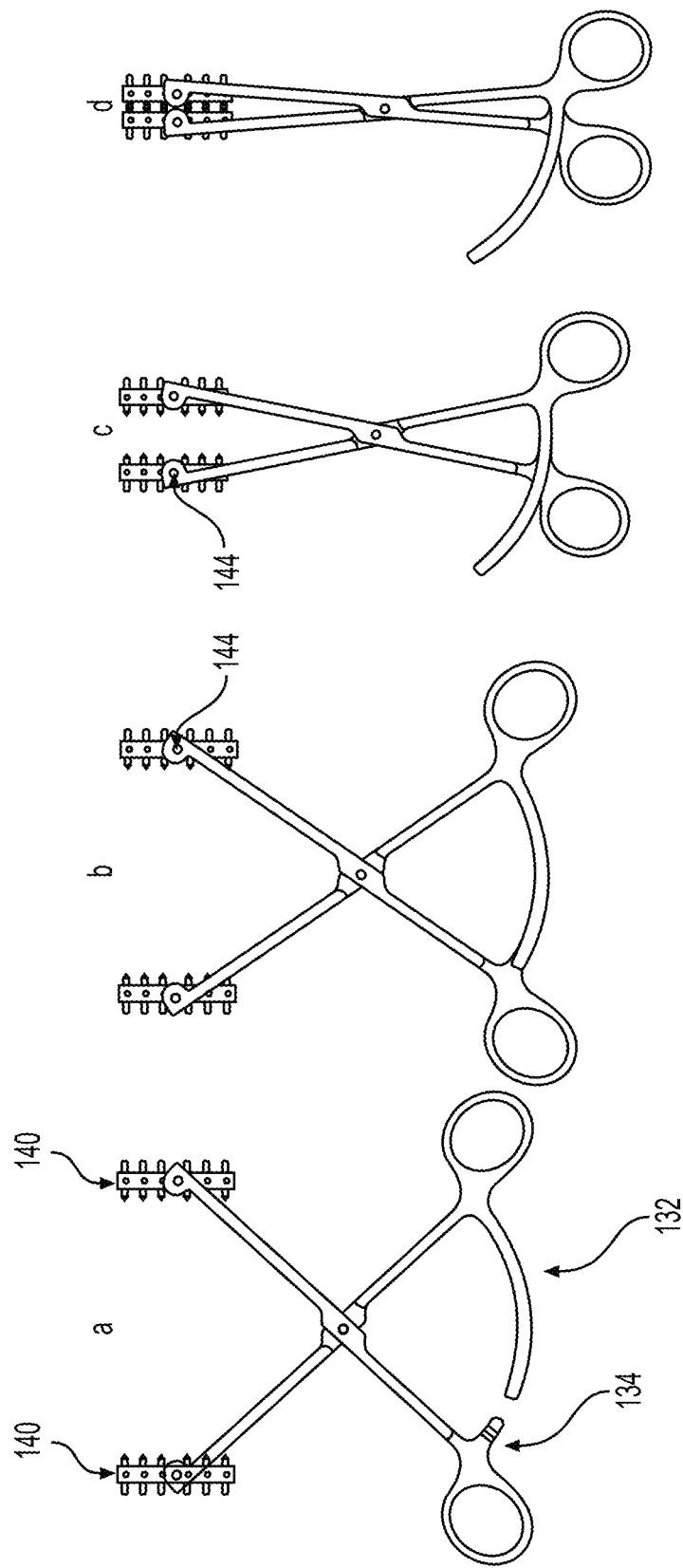
FIG. 3D illustrates the approximation of the distal ends of a first scissors arm and a second scissors arm of an exemplary tissue approximation device from a fully opened position (a) to a fully closed position (d).

As shown in FIG. 3A, in some embodiments, tissue approximation device 100 includes a ratchet 130 at the proximal ends of the first scissors arm 110 and the second scissors arm 120. The rachet 130 allows the approximation of the distal ends 114 of the first scissors arm 110 and the second scissors arm 120 to be flexibly adjusted across a range of distance. In some embodiments, as shown in FIG. 3D, the ratchet 130 includes a plurality of successive rachet teeth 132 and a ratchet catch 134. When the ring handles 112 are brought together, the ratchet catch 134 engages with and moves along the rachet teeth 132. The rachet catch 134 can be stopped at a desired position along the rachet teeth 132. In some embodiments, when the distal ends 114 of the first and second scissors arm 110 and 120 are spaced a part at a desired distance, the engagement of the ratchet catch 134 and the ratchet teeth 132 can be locked. In some embodiments, successive rachet teeth 132 are spaced apart at a fixed distance from each other. In some embodiments, successive rachet teeth 132 are closely spaced apart to allow flexible adjustment of the distance between the distal ends 114 of the first and second scissors arm 110 and 120.

In some embodiments, the rachet 130 is located at or near the end of the proximal ends of the first and second scissors arm 110 and 120. For example, as shown in FIG. 3B, the rachet 130 is at the end of the ring handles 112. In some embodiments, instead of the ratchet 130, the tissue approximation device 100 includes a screw locking mechanism 150 for adjustably locking the distance between the distal ends 114 of the first scissors arm 110 and the second scissors arm 120. In some embodiments, for example, as shown in FIG. 3C, the screw locking mechanism 150 includes a threaded shaft. The threaded shaft may have a first end attached to the first scissors arm 110 and a second end that passes through a hole in the second scissors arm 120. In some embodiments, the screw locking mechanism 150 further includes a locking screw. In some embodiments, the locking screw is threaded and configured to move along the threaded shaft to adjust the distance between the handles of the first and second scissors arms 110 and 120.

In some embodiments, as shown in FIG. 3A, to engage and grip tissue, a rake member 140 is connected to the distal end 114 of the first scissors arm 110. In some embodiments, a rake member 140 is connected to the distal end 114 of the first scissors arm 110 and a clamp member is at the distal end 114 of the second scissors arm 120. The clamp member may be a flat or curved plate integral to, fixedly connected, or removably connected to the distal end 114 of the second scissors arm 120. In some embodiments, two rake members 140 are respectively connected to the distal ends 114 of the first scissors arm 110 and the second scissors arm 120. In some embodiments, the rake members 140 are configured to grip tissue in an atraumatic fashion and bring the two gripped sides of tissue together. As defined herein, a rake member refers to a structural member that is permanently or removably attached to the distal end of a scissors arm via an articulating joint and includes an array of hooks configured to grip tissue.

In some embodiments, separating the ring handles 112 separates the rake members 140. In such embodiments, the ring handles 112 are approximated and brought together such that the rake members 140 are brought together to approximate two sides of tissue gripped by the rake members 140. In other embodiments, bringing the ring handles 112 together separates the rake members 140. In such embodiments, the ring handles 112 are moved apart from each together so that the rake members 140 are brought together to approximate the two sides of tissue gripped by the rake members 140.

As shown in FIG. 3A, in some embodiments, the rake member 140 includes one or more hooks 142 to grip or "bite" the tissue. In some embodiments, each hook 142 on the rake member 140 of the first scissors arm 110 corresponds to a hook 142 on the rake member 140 of the second scissors arm 120. For example, each hook 142 on the rake member 140 of the first scissors arm 110 is opposite to a hook 142 on the rake member 140 of the second scissors arm 120 to grip two opposite sides of tissue. In some embodiments, the hooks 142 are distributed in a linear fashion on the rake member 140. In some embodiments, the hooks 142 are distributed in two dimensions on the rake member 140. In such embodiments, the hooks 142 may be distributed in a plurality of rows, and in some embodiments in a plurality of staggered rows.

As described herein, any suitable number of hooks 142 may be mounted on the rake member 140. For example, the number of hooks 142 may be any number equal to or greater than three, e.g., three, four, five, six, seven, eight, etc. The number of hooks 142 may be determined based on the length of the rake member 140 and the distance between the hooks 142, which may be determined based on various considerations, such as the type, size, and/or location of the tissue to be gripped.

Figure 5B:
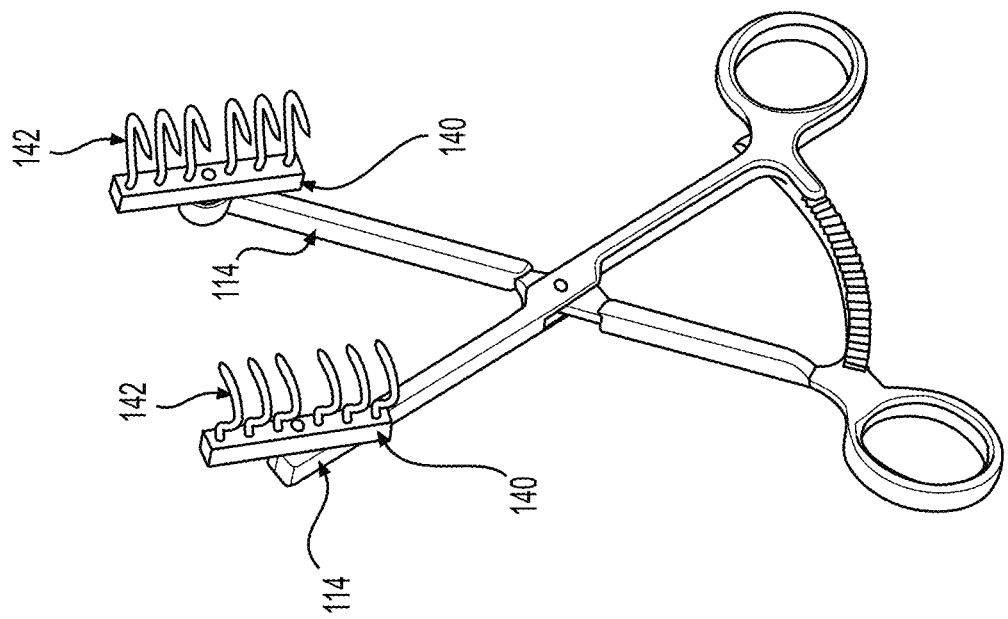
FIG. 5B illustrates a perspective view of the exemplary tissue approximation device of FIG. 5A.
Figure 5A:
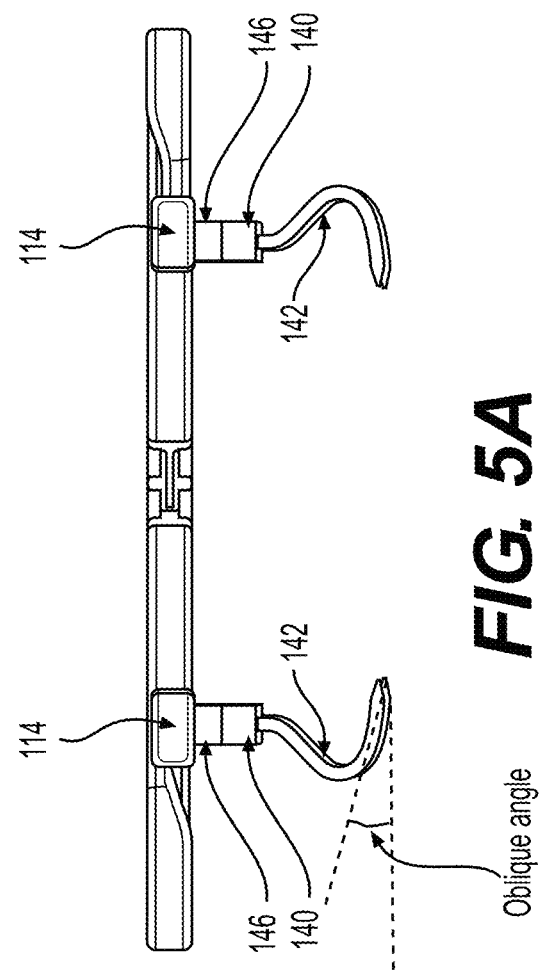
FIG. 5A illustrates a front view of an exemplary tissue approximation device, according to some embodiments of the present disclosure.

The hook 142 may have any suitable shape, size, and cross-section that allow the hook 142 to effectively grip the tissue, but not cut or slice through the tissue as the hook 142 applies pressure on it. In some embodiments, the hook 142 has an elongated body. The elongated body can be straight or curved. In some embodiments, the hook 142 has a cross-section with a curved or smooth circumference. In some embodiments, the hook 142 has a cross-section without a sharp edge. In some embodiments, the hook 142 has a cross-section without a cutting edge. For example, in some embodiments the hook 142 has a cross-section having a circular or elliptical circumference. In some embodiments, the hook 142 has a pointed tip. In some embodiments, the pointed tip is a cone-shaped pointed tip. In some embodiments, the hook 142 has a blunt or a semi-blunt tip. In some embodiments, the cross-section of the hook 142 is dimensioned to prevent the hook 142 from cutting through the tissue. In some embodiments, the dimeter of the cross-section of the hook 142 ranges from 0.8 mm to 1.5 mm FIG. 4A illustrates a front view of an exemplary tissue approximation device 100, according to some embodiments of the present disclosure. FIG. 4B illustrates a perspective view of the exemplary tissue approximation device 100 of FIG. 4A. FIG. 5A illustrates a front view of another exemplary tissue approximation device 100, according to some embodiments of the present disclosure. FIG. 5B illustrates a perspective view of the exemplary tissue approximation device of FIG. 5A.

As shown in FIGS. 4A-5B, in some embodiments, a portion of the elongated body of the hook 142 is curved or bent. In some embodiments, the entire length of the elongated body of the hook 142 is curved or bent. In some embodiments, as shown in FIGS. 4A and 5B, the curved or bent shape of the elongated body of the hook 142 allows the pointed tip of the hook 142 to penetrate and/or "bite" the tissue at an oblique angle. As defined herein and shown in FIG. 5A, the term "oblique angle" refers to the angle at which the hook 142 penetrates tissue to the plane of the first and second scissors arms 110 and 120.

In some embodiments, the curved or bent shape of the elongated body of the hook 142 allows the hook 142 to have a cupping effect to effectively grip the tissue. In some embodiments, as shown in FIGS. 4A and 5A, the shape of the elongated body of the hook 142 is designed in the shape of an inverted question mark. In some embodiments, the hook 142 is designed in the shape of the letter "C." The opening of the "C" may be tilted at different angles relative to the plane of the tissue being gripped. In some embodiments, the oblique angle of penetration allows the hook 142 to penetrate and grip the tissue, but not to tangentially scratch, and not to cut through or rip the tissue. In some embodiments, the oblique angle of penetration prevents the pointed tip of the hook 142 from penetrating the tissue perpendicularly wherein hook 142 may act like a straight rod tearing through the tissue. In some embodiments, the oblique angle of penetration further prevents the pointed tip of the hook 142 from perpendicularly penetrating and gripping the tissue with excessive torque, which may bend the hook 142 outward and cause it to pull out of the tissue, failing its attempt to bring the tissue together. In some embodiments, the oblique angle ranges from 15 degrees to 70 degrees. In some embodiments, as shown in FIGS. 4A and 5A, a hook 142 on the rake member 140 of the first scissors arm 110 and a corresponding hook 142 on the rake member 140 of the second scissors arm 120 form a pair and are curved inwardly towards each other.

Figure 6:
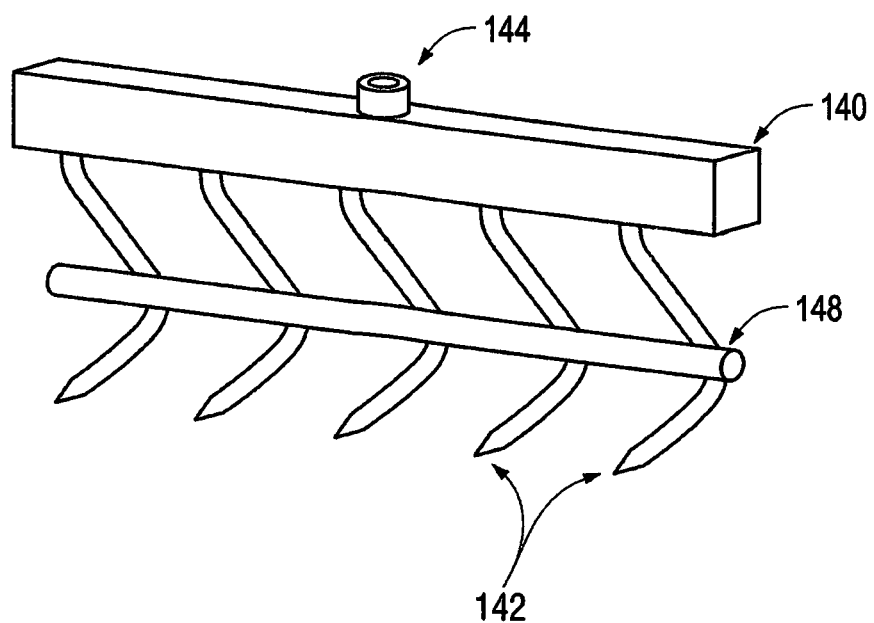
FIG. 6 illustrates a perspective view of an exemplary rake member of an exemplary tissue approximation device, according to some embodiments of the present disclosure.

FIG. 6 illustrates a perspective view of an exemplary rake member 140, according to some embodiments of the present disclosure. As shown in FIG. 6, in some embodiments, a transverse bar 148 connects the hooks 142 mounted on the rake member 140. The transverse bar 148 may be a rod or a tube. The transverse bar may be made of metal, plastic, or rubber. In some embodiments, the transverse bar 148 connects to the hooks 142 at the elbow flexion of the hooks 142. In some embodiments, the transverse bar 148 forms a ridge on the hooks 142 and limits the penetration of the hooks 142 into the tissue. In some embodiments, when the hooks 142 penetrate the tissue, the transverse bar 148 functions as a stop and rests against the surface of the tissue. The transverse bar 148 may relieve the tension on the hooks 142 penetrating and gripping the tissue by transferring and distributing the tension more evenly over a wider surface contacting the tissue.

In some embodiments, instead of connecting to the transverse bar 148, the hook 142 has a thickened portion along its shaft that functions as a stop to limit the penetration of the hook 142 into the tissue. In some embodiments, the thickened portion is a section along the length of the hook 142. The thickened portion may be in any suitable shape, such as a ball, a ridge, or a bar. In some embodiments, the thickened portion is formed by connecting to a separate member, such as a ball, a ridge, or a bar. The thickened portion may be placed at any suitable location along the length of the hook 142. In some embodiments, the thickened portion is formed at the elbow flexion of the hooks 142. In some embodiments, each of the hooks 142 of the rake member 140 includes a thickened portion.

The hook 142 and rake member 140 may be made of any suitable medical grade material. The rake member 140 may be disposable, replaceable, and reusable. In some embodiments, the rake member 140 comprises a locking mechanism that allows it to be replaced on the scissors arm. In some embodiments, the rake member 140 may be repeatedly disinfected and sterilized. The hook 142 may be disposable, replaceable, and reusable. In some embodiments, the hook 142 may be repeatedly disinfected and sterilized. In some embodiments, the rake member 140 and/or the hook 142 are made of surgical stainless steel. In some embodiments, the rake member 140 and/or hook 142 are made of surgical carbon steel. In some embodiments, the rake member 140 and/or hook 142 are made of medical grade polymeric material.

In some embodiments, as shown in FIG. 3A, the distal end 114 of the first scissors arm 110 is connected to a rake member 140 via an articulating joint 144. In some embodiments, each of the distal ends 114 of both the first scissors arm 110 and the second scissors arm 120 is connected to a rake member 140 via an articulating joint 144. In some embodiments, articulating joint 144 is a hinge joint or a pivot joint at the tip of distal end 114. FIG. 3D illustrates the approximation of the distal ends 114 of the first scissors arm 110 and the second scissors arm 120 from a fully opened position (a) to a fully closed position (d). As illustrated in FIG. 3D, as the distal ends 114 of the first scissors arm 110 and the second scissors arm 120 approximate, the articulating joints 144 allow the rake member 140 connected to the first scissors arm 110 and the rake member 140 connected to the second scissors arm 120 to stay parallel to each other and stay perpendicular to the direction of approximation. In some embodiments, the articulating joints 144 allow the wound edges to stay parallel while the first scissors arm 110 and the second scissor arm 120 are approximated at an angle.

In some situations, the articulating joints 144 may reduce or prevent the rake member 140 of the first scissors arm 110 and the rake member 140 of the second scissors arm 120 from forming a wedge arc that pinches the tissues at a variable angle in a scissor like fashion when the distal ends 114 of the first scissors arm 110 and the second scissors arm 120 approximate.

As shown in the front views of the exemplary tissue approximation device 100 of FIGS. 4A and 5A, in some embodiments, the hooks 142 and rake members 140 are in a plane below first and second scissors arms 110 and 120. Such configuration allows the other portions of tissue approximation device 100 to be out of the plane of the tissue being gripped and approximated by the hooks 142 and rake members 140. Such configuration further allows flexibility in adjusting the position of the tissue being gripped and approximated.

In some embodiments, as shown in FIGS. 4A and 4B, the distal ends 114 are curved and deviate from the plane of the other portions of first scissors arm 110 and second scissors arm 120. In such embodiments, as shown in FIG. 4A, the curved distal ends 114 position the rake members 140 below the plane of the other portions of the first scissors arm 110 and the second scissors arm 120. In some embodiments, the curved distal ends 114 position the hooks 142 and rake members 140 in a plane 1.5 cm to 4 cm below the plane of the first scissors arm 110 and the second scissors arm 120. For example, the curved distal ends 114 may position the hooks 142 and/or rake members 140 in a plane 1.5 cm, 2 cm, 2.5 cm, 3 cm, or 3.5 cm below the plane of the first scissors arm 110 and the second scissors arm 120. In some embodiments, the curved distal ends 114 enable adjusting the gripping or the position of the gripping of the tissue without interference from other portions of the tissue approximate device 100.

In some embodiments, as shown in FIGS. 5A and 5B, the distal ends 114 are flat and are in the same plane as the other portions of the first scissors arm 110 and second scissors arm 120. In such embodiments, as shown in FIG. 5A, the tissue approximation device 100 may further include vertical extension members 146 that protrude from the distal ends 114 of the first and second scissors arms 110 and 120 in a direction perpendicular to the plane of the distal ends 114. The vertical extension members 146 position the rake members 140 below the plane of the first scissors arm 110 and the second scissors arm 120. In some embodiments, the vertical extension members 146 position the hooks 142 and rake members 140 in a plane 1.5 cm to 4 cm below the plane of the first scissors arm 110 and the second scissors arm 120. For example, the vertical extension members 146 may position the hooks 142 and/or rake members 140 in a plane 1.5 cm, 2 cm, 2.5 cm, 3 cm, or 3.5 cm below the plane of the first scissors arm 110 and the second scissors arm 120. The vertical extension members 146 further allow adjusting the gripping or the position of the gripping of the tissue without interference from other portions of the tissue approximation device 100.

In some embodiments, in addition to or instead of using the tissue approximation device 100, internally induced tumescence is performed to place a tissue under tension for performing PME. In some embodiments, internally induced tumescence is achieved by injecting a material into the tissue in the area of interest. The material may include normal physiologic solutions, regenerative reagents, a suspension of cells, a tissue graft, or a selected combination thereof. In some embodiments, injecting the material separates the native fibers in the tissue, thereby generating a fibrous vascularized scaffold with interstices that can be filled by new tissue generated from the natural regenerative process of tissue. In some embodiments, a material having regenerative potential is injected into the interstices to further promote tissue regeneration and expansion.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. Moreover, while illustrative embodiments have been described herein, the scope of the disclosure includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

It is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as exemplary only, with a true scope and spirit of the disclosed embodiments being indicated by the following claims.

What is claimed is:

1. A tissue approximation device to place tissue under tension comprising:
   a first arm having a proximal end and a distal end;
   a second arm having a proximal end and a distal end, the second arm being connected to the first arm; and a first rake member connected to the distal end of the first arm, the first rake member comprising a plurality of tissue engaging members configured to grip tissue without slicing through tissue; and a second rake member connected to the distal end of the second arm, the second rake member comprising a plurality of tissue engaging members configured to grip tissue; and a first transverse bar connected to the tissue engaging members of the first rake member and a second transverse bar connected to the tissue engaging members of the second rake member, the first and second transverse bars limiting penetration of the tissue engaging members into tissue.

2. The tissue approximation device of claim 1, wherein the first rake member and the second rake member move towards each other in parallel as the distal ends of the first arm and the second arm approximate.

3. The tissue approximation device of claim 2, wherein the first and second arms close in a scissors like fashion.

4. The tissue approximation device of claim 2, further comprising a retaining structure to retain the first and second arms in a position with the first and second rake members approximated.

5. The tissue approximation device of claim 1, wherein movement of the first and second arms move the first and second rake members, the first and second rake members staying parallel to each other and perpendicular to a direction of approximation during such movement.

6. The tissue approximation device of claim 1, wherein the tissue engaging members comprise hooks, and at least a portion of the hooks has an elongated body is curved to penetrate tissue at an oblique angle.

7. The tissue approximation device of claim 1, wherein the distal end of the first arm is in the same plane as the other portions of the first arm.

8. The tissue approximation device of claim 1, further comprising a vertical extension member attached to the distal end of the first arm that positions the first rake member below a plane of the first arm.

9. The tissue approximation device of claim 1, wherein the distal end of the first arm is in a different plane than other portions of the first arm.

10. The tissue approximation device of claim 1, wherein the first rake member is connected to the distal end of the first arm via a first articulating joint and the second rake member is connected to the distal of the second arm via a second articulating joint, wherein the first and second articulating joints are configured to cause the first rake member and the second rake member to move towards each other in parallel as the distal ends of the first arm and the second arm approximate.

11. The tissue approximation device of claim 1, wherein the transverse bars relieve tension on the tissue engaging members by transferring tension to tissue more evenly over a wider surface contacting tissue.

12. The tissue approximation device of claim 1, wherein the first rake member is removably and replaceably connected to the first arm.

13. The tissue approximation device of claim 1, wherein the tissue engaging members comprise hooks having curved distal ends to position the hooks in a plane between 1.5 cm and 4 cm below the plane of the first arm.

14. The tissue approximation device of claim 1, wherein the first rake member is positioned below a plane of the first arm.

* * * * *